United States Patent [19]

Bridges

[11] Patent Number: 4,462,686
[45] Date of Patent: Jul. 31, 1984

[54] LASER ISOTOPE DETECTION AND MEASUREMENT

[75] Inventor: Thomas J. Bridges, Holmdel, N.J.

[73] Assignee: AT&T Bell Laboratories, Murray Hill, N.J.

[21] Appl. No.: 252,407

[22] Filed: Apr. 9, 1981

[51] Int. Cl.³ .......................................... G01N 21/64
[52] U.S. Cl. ................................. 356/318; 250/458.1
[58] Field of Search .............. 356/301, 317, 318, 417; 250/302, 303, 458.1, 459.1, 461.1, 461.2

[56] References Cited

U.S. PATENT DOCUMENTS 3,936,190  2/1976  Ohnishi et al. ..................... 356/318
4,068,953  1/1978  Harney et al. ..................... 356/301
4,188,120  2/1980  McDonald et al. ......... 250/459.1 X

FOREIGN PATENT DOCUMENTS 37087  3/1977  Japan ................................. 356/301

OTHER PUBLICATIONS

Herriott et al., *Applied Optics*, vol. 4, No. 8, Aug. 1965, pp. 883-889.
Freed et al., *Journal of Molecular Spectroscopy*, vol. 49, 1974, pp. 439-453.
Wood et al., *Optics Letters*, vol. 5, No. 4, Apr. 1980, pp. 153-154.

*Primary Examiner*—F. L. Evans
*Attorney, Agent, or Firm*—Michael B. Einschlag; Daniel D. Dubosky; Wendy W. Koba

[57] ABSTRACT

The present invention relates to an apparatus for laser isotope detection and concentration measurement (LIDAM). A test sample containing first and second isotopes of a specific material or compounds formed with the first and second isotopes of the specific material is placed in an optical bridge with a standard sample containing known amounts of the first and second isotopes or compounds of the same. Laser radiation from a first and a second laser source is alternatively focused upon the two samples to produce fluorescence from the isotopes or compounds of the specific material. The laser material of the first laser source and the laser material of the second laser source are either the first and the second isotope respectively or compounds formed with the first and the second isotope respectively. Laser radiation from the first and the second laser source induces fluorescence only from the first and second isotope or compounds of the same in either the test or standard sample. The characteristic fluorescences induced are detected and used to determine the relative ratios of the first and second isotopes or compounds of the same in the test sample.

12 Claims, 4 Drawing Figures

LASER ISOTOPE DETECTION AND MEASUREMENT

BACKGROUND OF THE INVENTION

The present invention pertains to the field of isotope detection.

The use of isotopes as tracers is wide spread in medicine and geophysics, but measurements are made with a mass spectrometer or by gas chromatography. These batch type measurements are made by highly skilled technicians in a laboratory and require a considerable length of time to complete. A portable instrument giving a direct reading and virtually instantaneous response would be desired.

SUMMARY OF THE INVENTION

The present invention relates to an apparatus for laser isotope detection and concentration measurement (LIDAM). A test sample containing first and second isotopes of a specific material or compounds formed with the first and second isotopes of the specific material is placed in an optical bridge with a standard sample containing known amounts of the first and second isotopes or compounds of the same. Laser radiation from a first and a second laser source is alternatively focused upon the two samples to produce fluorescence from the isotopes or compounds of the specific material. The laser material of the first laser source and the laser material of the second laser source are either the first and the second isotope respectively or compounds formed with the first and the second isotope respectively. Laser radiation from the first and the second laser source induces fluorescence only from the first and second isotope or compounds of the same, respectively, in either the test or standard sample. The characteristic fluorescences induced are detected and used to determine the relative ratios of concentrations of the first and second isotopes or compounds of the same in the test sample.

In one embodiment of the present invention, the detection of carbon isotopes in the form of carbon dioxide is achieved by utilizing carbon dioxide lasers, one utilizing carbon dioxide formed from a first isotope of carbon and the other laser using carbon dioxide formed from another isotope of carbon.

BRIEF DESCRIPTION OF THE DRAWING

A complete understanding of the present invention may be gained from a consideration of the detailed description presented hereinbelow in connection with the accompanying drawings in which.

DETAILED DESCRIPTION

The present invention is an apparatus for using laser radiation to detect and measure ratios of concentrations of isotopes or compounds formed from isotopes of specific materials. In particular, the following will describe the present invention as it pertains to a particular embodiment, i.e. that of detecting ratios of $^{12}C$ and $^{13}C$.

In geology and medicine a measurement is commonly made of the small changes or variations of the proportion of the concentrations of $^{13}C/^{12}C$ in rocks and in living matter. The standard of $^{13}C/^{12}C$ ratio of concentrations is called the Pee Dee Belemite (PDB) standard and $^{13}\Delta C$ is designated as $$^{13}\Delta C \text{ (per mil)} = \left[ \frac{(^{13}C/^{12}C) \text{ sample}}{(^{13}C/^{12}C) \text{ PDB}} - 1 \right] \times 10^3. \tag{1}$$

Figure 2:
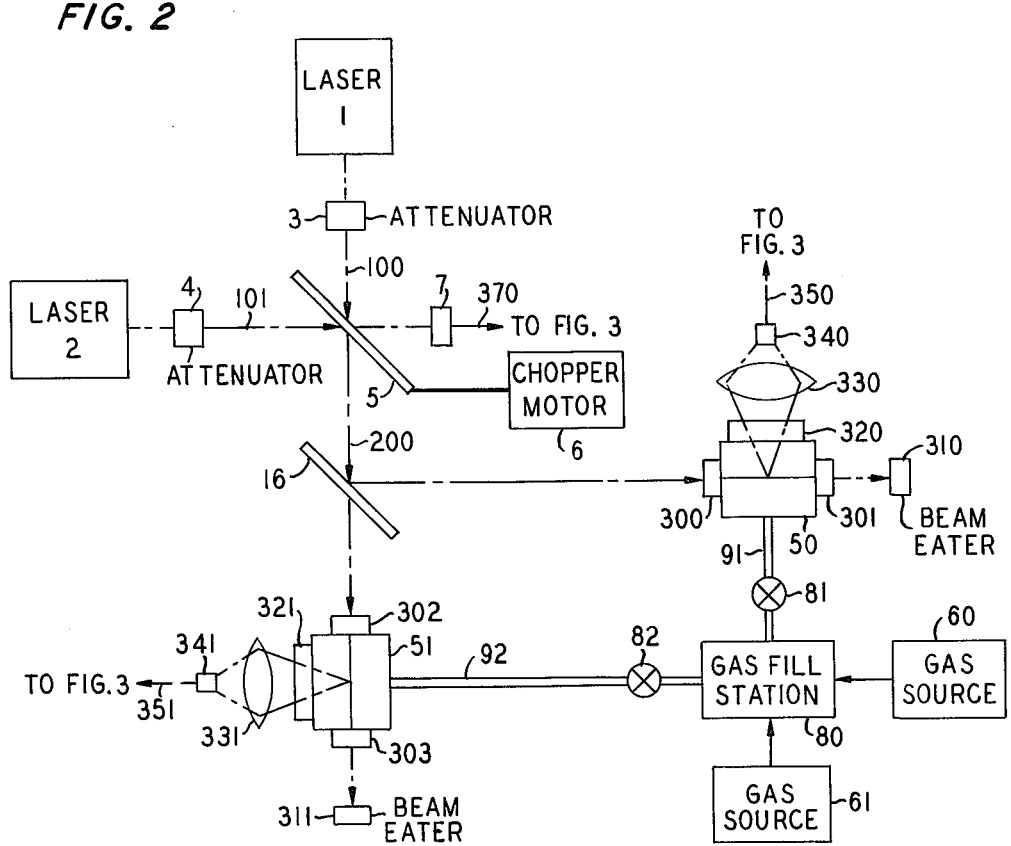
FIGS. 2 and 3 show, in pictorial form, an embodiment of the present invention for determining the relative concentrations of $^{12}C^{16}O_2$ and $^{13}C^{16}O_2$ in a gas.

The embodiment of FIG. 2, constructed according to the present invention, measures this factor by comparing an unknown test sample with a standard sample of isotopic compounds of $CO_2$ in an optical bridge. Although there are many different arrangements which are possible to be constructed according to the present invention, the embodiment shown in FIG. 2 has the advantage of compensating for fluctuations of laser power from the laser sources.

At the heart of the present invention, is the fact that a $CO_2$ laser will operate with several isotopic compounds of $CO_2$ as the lasing material, oscillation occurring on the $00°1 \rightarrow 10°0$, $02°0$ vibrational-rotational bands near 10 μm. These oscillating transitions are automatically lined up spectrally with the corresponding absorption lines of the same isotopic compound of $CO_2$ in the test sample to be measured. Absorption of the laser radiation is detected by observing the fluorescence induced in the particular isotopic $CO_2$ compound, which induced fluorescence occurs at about 4.3 μm.

Figure 1:
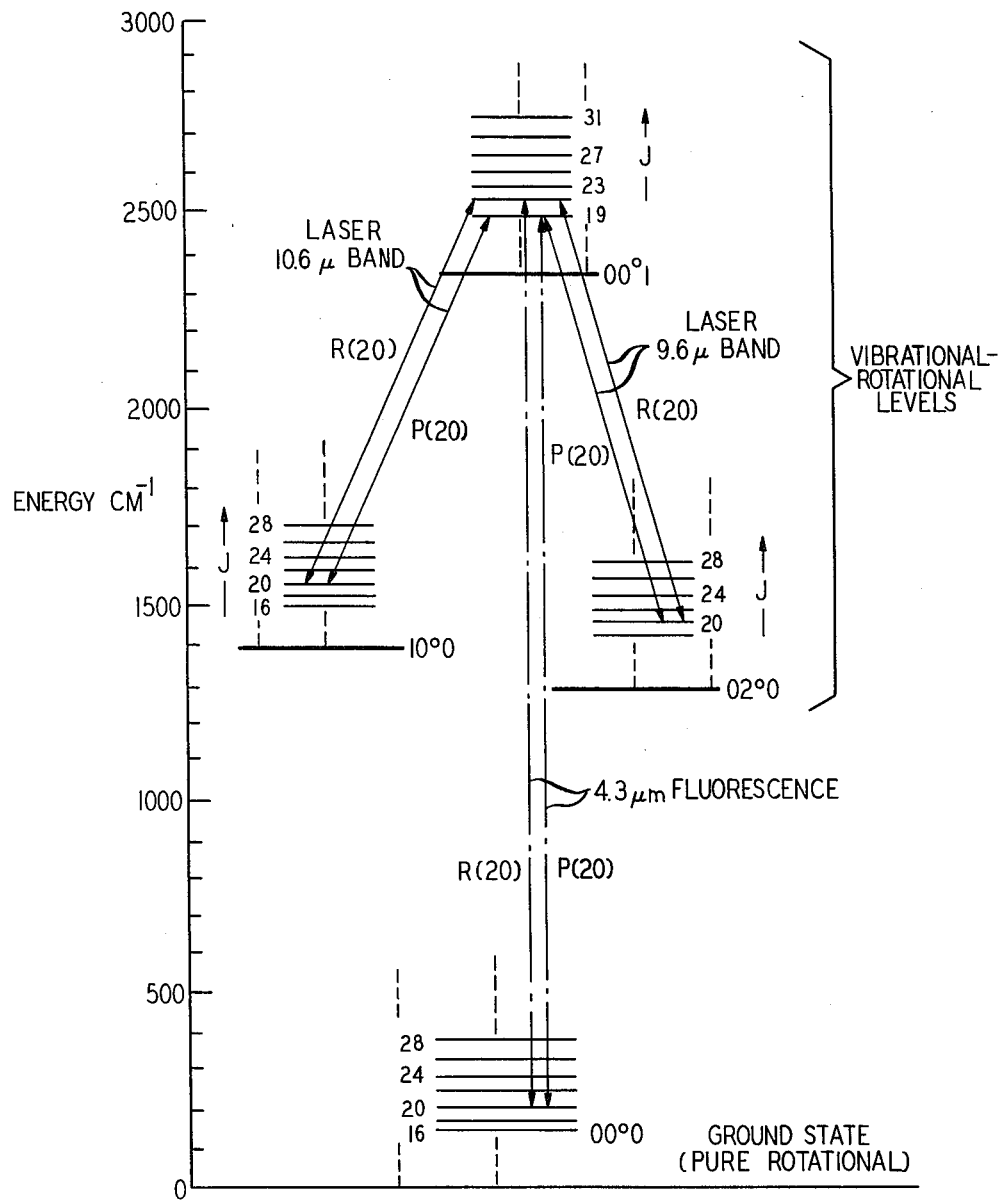
FIG. 1 shows, in diagramatic form, some of the energy levels of a carbon dioxide molecule.

FIG. 1 shows a diagram of the energy levels of the $CO_2$ molecule that are involved. At room temperature, the $10°0$ and $02°0$ levels of the $CO_2$ molecule are partially populated thermally and the $00°1$ level is considerably less populated. Absorption of $CO_2$ laser radiation by the $CO_2$ gas, which absorption can arise from many vibrational-rotational transitions, will produce transitions from the $02°0$ or $10°0$ level to the $00°1$ level. (As shown in FIG. 1.) The $CO_2$ molecules will then decay to the ground state, $00°0$, spontaneously while emitting incoherent radiation at approximately 4.3 μm. The transition probability of the $00°1 \rightarrow 00°0$ transitions greatly exceeds that of any other transitions from the $00°1$ level, so that radiative transitions occur predominantly on those lines. Note that the excitation of the $CO_2$ molecule decays by collisions with cell walls and other molecules as well as by radiative decay. This establishes gas pressure to be an important factor, which factor will be discussed hereinbelow.

The laser induced fluorescence at approximately 4.3 μm is a measure of the $CO_2$ gas present and is extremely selective as to isotope. Because of the isotopic frequency shift of molecule vibrations, the radiation from a $^{12}C^{16}O_2$ laser will only produce fluorescence in $^{12}C^{16}O_2$ gas whereas radiation from a $^{13}C^{16}O_2$ laser will only excite fluorescence in $^{13}C^{16}O_2$. Since lasing has been obtained in many of the combinations of $^{12}C$, $^{13}C$, $^{14}C$ and $^{16}O_2$, and $^{18}O_2$, as shown in an article entitled, "Determination of Laser Line Frequencies and Vibrational-Rotational Constants of the $^{12}C^{18}O_2$, $^{13}C^{16}O_2$, and $^{13}C^{18}O_2$ Isotopes from Measurements of CW Beat Frequencies with Fast HgCdTe Photodiodes and Microwave Frequency Counters", *Jrnl. of Molecular Spectroscopy*, Vol. 49, 1974, pp. 439-453, by C. Freed, A. H. M. Ross and R. G. O'Donnell, the apparatus discussed hereinbelow provides a means for detecting and measuring the isotopes of O as well as those of C. Clearly the invention covers isotopes of O such as 170 other than those explicitly mentioned above.

FIG. 2 shows an optical bridge apparatus. Laser source 1 is a $^{12}C^{16}O_2$ laser and laser source 2 is a $^{13}C^{16}O_2$ laser. (Both lasers may be single line, grating controlled to enhance the spectral purity of their output.) Attenuator 3 and attenuator 4 may be used to help match the intensity of laser radiation from laser source 1 and laser source 2.

A mirror chopper comprising mirror 5 and chopper motor 6 alternates the simultaneous application of either $^{12}C^{16}O_2$ or $^{13}C^{16}O_2$ laser radiation to both the test sample and the standard sample. The alternation of the application of laser radiation minimizes the effects of laser power fluctuations. Detector 7 absorbs radiation from laser beam 100 or laser beam 101 and produces gate signal 370.

Beam 200, alternately comprising radiation from beam 100 or beam 101, is split by 50 percent broadband beam splitter 16 so that radiation from beam 200 simultaneously impinges upon the test and sample cells.

Test cell 50 contains the unknown sample of gas, which sample of gas is supplied to test cell 50 from gas source 60, via gas fill station 80, valve 81 and gas fill line 91.

Sample cell 51 contains the known sample of gas, which sample of gas is supplied to sample cell 51 from gas source 61 via gas fill station 80, valve 82 and gas fill line 92.

The laser entrance and exit of test cell 50 and sample cell 51 are fitted with windows 300-303, which windows are transparent to radiation near 10 μm. Illustratively, these windows may be fabricated out of NaCl or ZnSe. Any excess laser radiation which is not absorbed in the test and sample cells is absorbed in absorbers 310 and 311 placed behind the cells.

The laser-induced fluorescence exits the cells through windows 320 and 321, which windows are transparent to radiation in the wavelength region 4-5 μm, but absorb scattered 10 μm radiation. Illustratively, these windows may be fabricated out of sapphire.

The laser-induced fluorescence passing through windows 320 and 321 is focused by lenses 330 and 331 onto photodetectors 340 and 341, illustratively InSb detectors. Photodetectors 340 and 341 produce electric signals 350 and 351 in response to the laser-induced flourescence passing through windows 320 and 321.

Figure 3:
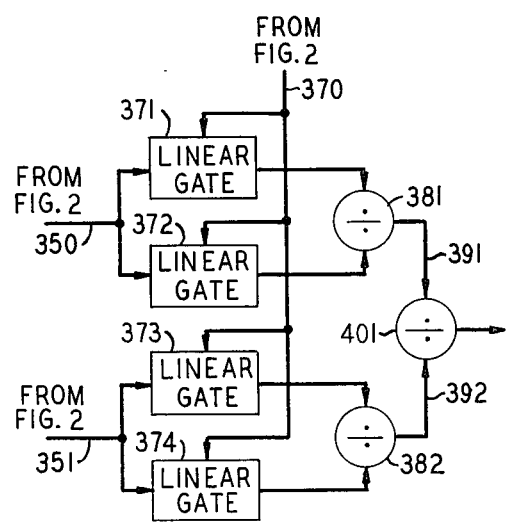

FIG. 3 shows an embodiment of an apparatus for utilizing electric signals 350 and 351 to analyze the isotopic concentrations. Linear gates 371-374 operate synchronously with the chopper signal 370. Gates 371 and 373 are set to be open when $^{12}CO_2$ laser radiation from beam 100 illuminates cells 50 and 51. Gates 372 and 374 are set to be open when $^{13}CO_2$ laser radiation from beam 101 illuminates cells 50 and 51.

The electric signals generated by linear gates 371 and 372 are fed into divider 381, which divider produces a signal which is proportional to the ratio of the amount of $^{12}CO_2$ and $^{13}CO_2$ in cell 50. The electric signals generated by linear gates 373 and 374 are fed into divider 382, which divider produces a signal which is proportional to the ratio of the amount of $^{13}CL_2$ and $^{12}CO_2$ in cell 51. The further analysis uses the following notation: $W_{12}(50)$, $W_{12}(51)$, $W_{13}(50)$, $W_{13}(51)$ are the powers of $^{12}CO_2$ laser radiation and $^{13}CO_2$ laser radiation incident on cells 50 and 51 respectively and $^{12}C(50)$, $^{12}C(51)$, $^{13}C(50)$, $^{13}C(51)$ are the concentrations of $^{12}CO_2$ and $^{13}CO_2$ in cells 50 and 51 respectively. Thus the electric signal 391 output from divider 381 is proportional to $[(W_{13}(50) \times ^{13}C(50)]/[(W_{12}(50) \times ^{12}C(50)]$ and electric signal 392 output from divider 382 is proportional to $[(W_{13}(51) \times ^{13}C(51)]/[(W_{12}(51) \times ^{12}C(51)]$. Electric signals 391 and 392 are input to divider 401. As a simplification consider the case where the powers in the two cells are equal, i.e. $W_{12}(50) = W_{12}(51)$ and $W_{13}(50) = W_{13}(51)$. Then the output from divider 401 is equal to:

$$R = [^{13}C(50)/^{12}C(50)]/[^{13}C(51)/^{12}C(51)] \quad (2).$$

If cell 51 contains the PDB standard then $^{13}\Delta C$ (per mil) $= (R-1) \times 10^3$. Note that for best accuracy in dividing, all the ratios should be near unity. This is achieved by making $W_{12}/W_{13}$ approximately equal to $^{13}C(50)/^{12}C(50)$ and approximately equal to $^{13}C(51)/^{12}C(51)$.

Figure 4:
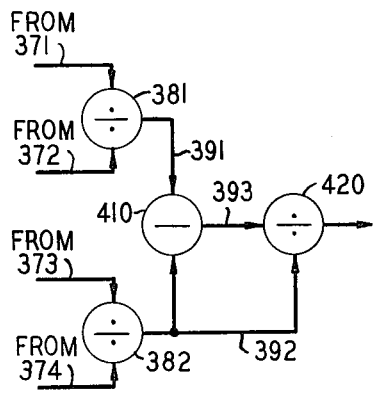
FIG. 4 shows, in diagramatic form, an embodiment of a circuit used with the embodiment of FIGS. 2 and 3.

Better accuracy may be achieved if divider 401 takes the ratio of the difference $(^{13}C(50)/^{12}C(50) - ^{13}C(51)/^{12}C(51))$ to $^{13}C(51)/^{12}C(51)$, giving the value of $^{13}\Delta C$ directly. This may be accomplished as shown in FIG. 4, by first subtracting electric signal 392 from electric signal 391 in subtractor 410 and inputting the subtraction signal and electric signal 392 to divider 420. Furthermore if the amount of fluorescence needs to be increased, a multiple transit cell such as a "White" cell (see pp. 347-348 in a book entitled "Concepts of Classical Optics", W. H. Freeman Co. by J. Strong) or a "Herriott" cell (see an article entitled "Folded Optical Delay Lines", *Appl. Optics*, Vol. 4, No. 8, August 1965, by D. R. Herriott and H. J. Schulte, pp. 883-889) could be used to hold the samples.

The pressure of the gases in the cells is important because the fluorescence increases with pressure, due both to the increase in molecular density and a decrease in wall deactivation. However at higher pressures volume deactivation due to molecular collisions and radiation trapping act to reduce the fluorescence. These counteracting effects lead to a maximum fluorescence yield at a pressure in the range of about 0.1 to 1 torr, depending on the geometry of the cell.

Furthermore, due to the fact that the absorbing transition (i.e. 10°0, 02°0→00°1) in the above-described embodiment is in a "hot" band, i.e., its lower state is not the ground state, any molecular population of the lower state results from thermal excitation from the ground state as expressed by the Boltzman factor $\exp(E/kT)$. This population and hence the absorption becomes very temperature sensitive. A cell heated to a few hundred degrees would result in a considerable increase in the fluorescence signal because of the increase in population of the lower state, either 10°0 or 02°0.

Carbon dating, i.e. measuring the ratio of $^{14}C/^{12}C$, may be performed in an embodiment of the present invention similar to that described above, by using a $^{14}C^{16}O_2$ laser.

It should be clear to those skilled in the art that the present invention is not restricted to detection of the isotopes of C and O. For example, the $N_2O$ laser operates in a strictly analogous manner to the $CO_2$ laser, thereby offering its use in detecting N isotopes, principally $^{15}N$. Another example is the use of a $CS_2$ laser for detecting S isotopes.

What is claimed is:

1. Apparatus for determining the ratio of concentrations of first and second isotopes of a specific material in a test sample which comprises:
- a standard sample containing a known ratio of concentrations of either said first and second isotopes or a compound containing said first and second isotopes of said specific material;
- a first source of laser radiation which utilizes a laser material comprising said first isotope or said compound of said first isotope;
- a second source of laser radiation which utilizes a laser material comprising said second isotope or said compound of said second isotope;
- means for alternatively exposing said test and said standard samples to said laser radiation from said first and said second sources, a portion of which radiation is absorbed in said test and said standard samples; and
- means for detecting the portion of said absorbed radiation and comparing the amounts absorbed from said first source and said second source, whereby said ratio is determined.

2. Apparatus in accordance with claim 1 wherein said means for detecting the portion of said absorbed radiation comprises means for detecting fluorescences from said test and said standard samples.

3. Apparatus in accordance with claim 2 wherein said means for detecting fluorescences comprises photodetector means disposed to absorb fluorescence from said test and said standard samples for producing electric signals responsive thereto; and
- means for analyzing said electric signals for providing said ratio in said test sample and said standard sample.

4. Apparatus in accordance with claim 3 wherein said means for analyzing said electric signals comprises means for detecting the presence of laser radiation from said first or said second laser source and providing a chopper electric signal in response thereto;
- a first, second, third and fourth linear gate, all of which operate synchronously with the application thereto of said chopper electric signal, said electric signal responsive to said florescence from said test cell is applied to said first and said second linear gates, said electric signal responsive to said florescence from said standard sample is applied to said third and said fourth gates, said first gate and said third gate are set to be opened when laser radiation from said first source illuminates said test and said standard sample and said second and said fourth gates are set to be opened when laser radiation from said second source illuminates said test and said standard samples;
- a first divider, to which is applied the output signals from said first and said second linear gates, for providing a first division signal proportional to the quotient of the applied output signals from said first and said second linear gates;
- a second divider, to which is applied the output signals from said third and said fourth linear gates, for providing a second division signal proportional to the quotient of the applied output signals from said second and said fourth linear gates; and
- means for analyzing said first and said second division signals for providing said ratio.

5. Apparatus in accordance with claim 4 wherein said means for analyzing includes a third divider, to which is applied said first and said second division signals, for providing the ratio of said first and said second division signals.

6. Apparatus in accordance with claim 4 wherein said means for analyzing includes subtractor means, to which is applied said first and said second division signals, for providing a subtraction signal substantially equal to the difference between said first and said second division signals; and a third divider, to which is applied said subtraction signal and said second division signal, for providing the ratio of said subtraction signal and said second division signal.

7. Apparatus in accordance with claim 3 wherein said first source is a $^{12}CO_2$ laser and said second source is a $^{13}CO_2$ laser.

8. Apparatus in accordance with claim 3 wherein said first source is a $C^{16}O_2$ laser and said second source is a $C^{18}O_2$ laser.

9. Apparatus in accordance with claim 3 wherein said first source is a $C^{16}O_2$ laser and said second source is a $C^{17}O_2$ laser.

10. Apparatus in accordance with claim 3 wherein said first source is a $^{12}CO_2$ laser and said second source is a $^{14}CO_2$ laser.

11. Apparatus in accordance with claim 3 wherein said first source is a $^{14}N_2O$ laser and said second source is a $^{15}N_2O$ laser.

12. Apparatus in accordance with claim 3 wherein said first source is a $C^{32}S_2$ laser and said second source is a $C^{33}S_2$ laser, or $C^{34}S_2$ or $C^{36}S_2$.

* * * * *